(12) United States Patent
Mulqueen et al.

(10) Patent No.: US 11,490,907 B2
(45) Date of Patent: Nov. 8, 2022

(54) INSTRUMENTS AND SYSTEMS FOR AN ORTHOPEDIC SHOULDER REPLACEMENT

(71) Applicant: Zimmer Biomet Pty Ltd, Belrose (AU)

(72) Inventors: Marika Mulqueen, Strathdale (AU); Massoud Akbarshahi, Belrose (AU)

(73) Assignee: Zimmer Biomet Pty Ltd, Belrose (AU)

( * ) Notice: Subject to any disclaimer, the term of this patent is extended or adjusted under 35 U.S.C. 154(b) by 98 days.

(21) Appl. No.: 17/089,361

(22) Filed: Nov. 4, 2020

(65) Prior Publication Data

US 2021/0128180 A1 May 6, 2021

Related U.S. Application Data

(60) Provisional application No. 62/931,482, filed on Nov. 6, 2019.

(51) Int. Cl.
*A61B 17/17* (2006.01)
*A61F 2/46* (2006.01)
*A61B 17/16* (2006.01)

(52) U.S. Cl.
CPC ...... *A61B 17/1778* (2016.11); *A61B 17/1684* (2013.01); *A61F 2/4612* (2013.01)

(58) Field of Classification Search
CPC . A61B 17/164; A61B 17/1742; A61B 17/175; A61B 17/15; A61B 17/1684; A61B 17/1778; A61F 2/4612
See application file for complete search history.

(56) References Cited

U.S. PATENT DOCUMENTS

2013/0096564 A1\* 4/2013 Winslow ............... A61B 17/15
606/96

\* cited by examiner

*Primary Examiner* — Samuel S Hanna
(74) *Attorney, Agent, or Firm* — Schwegman Lundberg & Woessner, P.A.

(57) ABSTRACT

An instrument assembly for a shoulder arthroplasty that can comprise: a cut guide having a slot for aiding a resection of a head of a humerus; and a positioning assembly configured to position the cut guide relative to the head of the humerus, wherein the positioning assembly is configured to couple to a reamer. The positioning assembly can comprise: a boom configured to position the cut guide relative to the reamer and the head of the humerus along a first axis; and an arm coupled to the cut guide and configured to be moveable to position the cut guide relative to the head of the humerus about the reamer in a second axis.

7 Claims, 18 Drawing Sheets

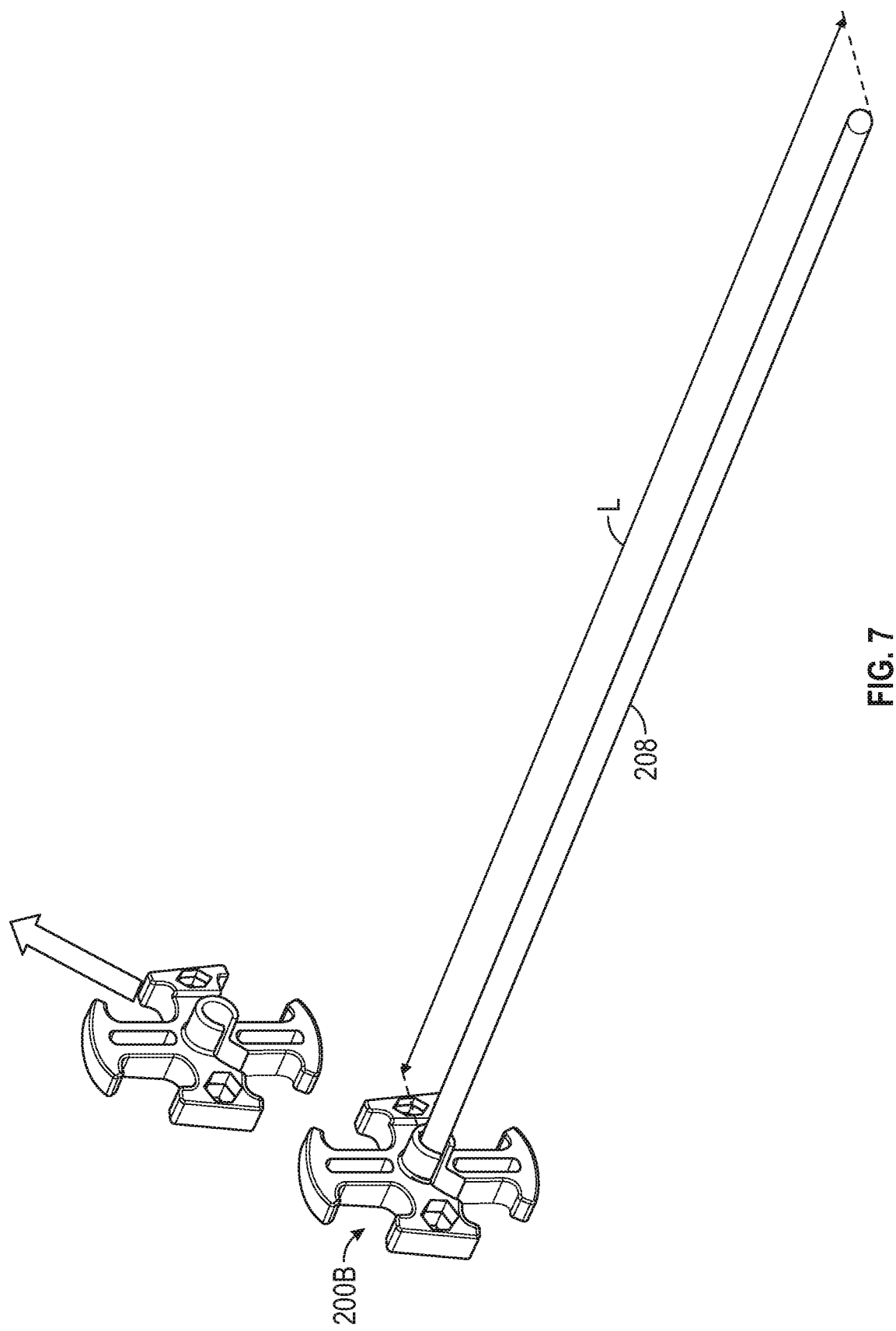

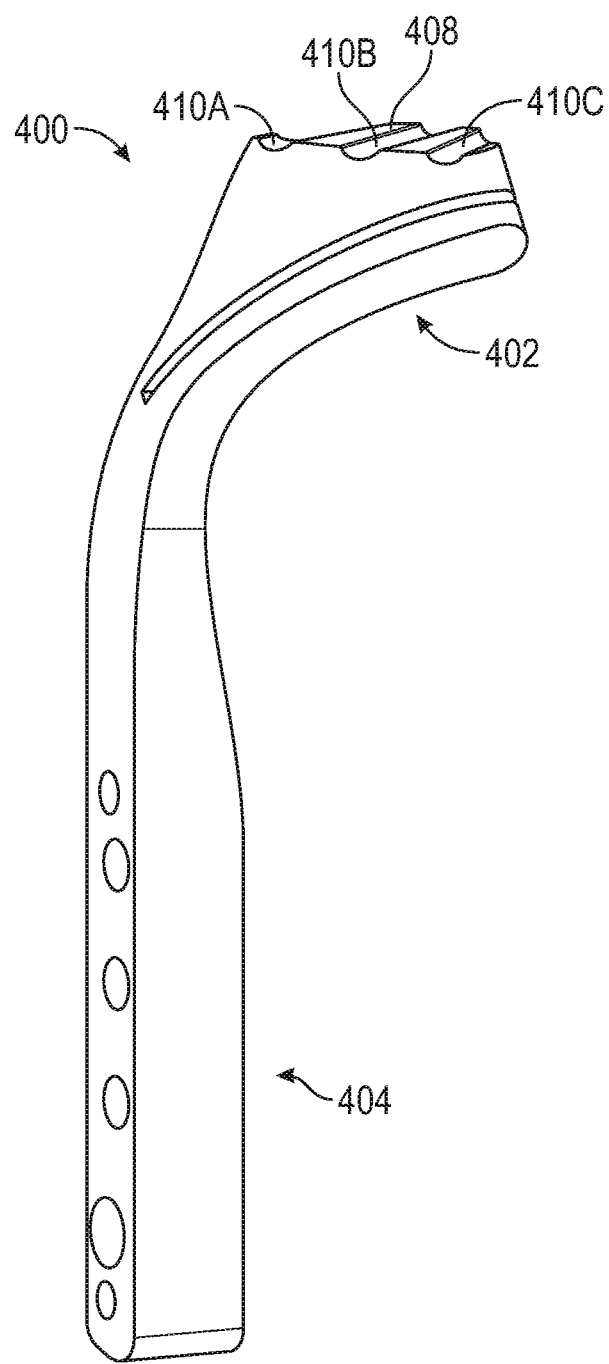
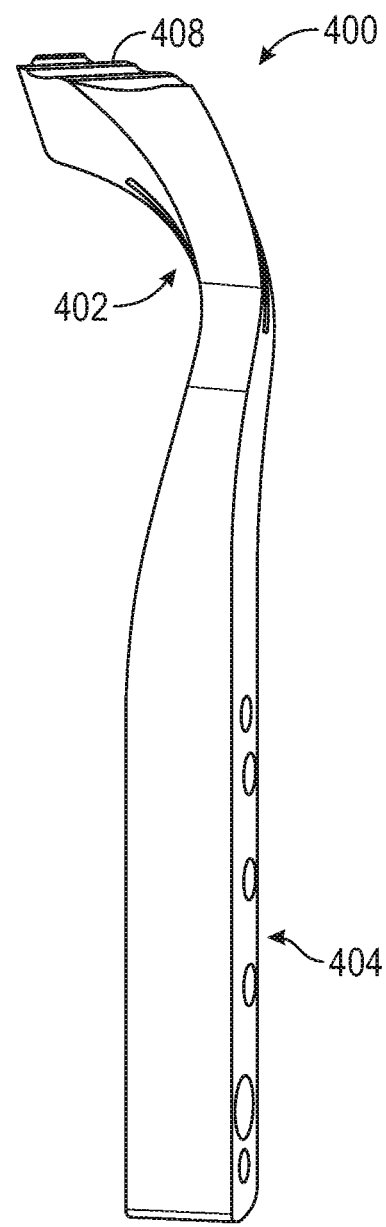
FIG. 10A
FIG. 10B

INSTRUMENTS AND SYSTEMS FOR AN ORTHOPEDIC SHOULDER REPLACEMENT

CLAIM OF PRIORITY

This application claims the benefit of U.S. Provisional Patent Application Ser. No. 62/931,482, filed on Nov. 6, 2019, the benefit of priority of which is claimed hereby, and which is incorporated by reference herein in its entirety.

BACKGROUND

The shoulder joint is a complex joint with the scapula, clavicle and the humerus all coming together to enable a wide range of movement, at least in a properly functioning joint. In a properly functioning shoulder joint the head of the humerus fits into a shallow socket in the scapula, typically referred to as the glenoid. Articulation of the shoulder joint involves movement of the humeral head in the glenoid, with the structure of the mating surfaces and surrounding tissues providing a wide range of motion.

The shoulder joint can undergo degenerative changes caused by various issues, such as rheumatoid arthritis, osteoarthritis, rotator cuff arthroplasty, vascular necrosis or bone fracture. When severe joint damage occurs and no other means of treatment is found to be effective, a total, partial, or reverse shoulder replacement or reconstruction may be necessary. Total shoulder replacements can involve a humeral prosthetic, including a stem and a head portion used to replace the natural humeral head. Total shoulder replacements will also typically involve resurfacing of the glenoid with a prosthetic implant. The glenoid implant generally will include an articulating cup shaped to receive the prosthetic humeral head. A reversal shoulder replacement (arthroplasty) involves a different set of humeral and glenoid replacement prosthetics. In a reverse shoulder the humeral component includes a cup shaped articular surface attached to a stem implanted into the humerus, while a spherical glenoid component is used to provide an articular surface for the humeral cup.

SUMMARY

Various techniques have been developed for resecting the humeral head to facilitate implantation of the humeral component. One such technique, called an minimally invasive surgery approach technique ("MIS") has been developed which provides a different access point for a surgeon to perform the resection of the humeral head from other techniques such as a standard superior approach technique. The object of the MIS technique is to avoid resection of the suprascapularis and infraspinatus muscles. One problem to be solved by the present systems and instruments is the limited access the surgeon has in performing resection of the humerus with the MIS technique. However, the present instruments and systems can provide the surgeon with more flexibility in repositioning a cut guide used in performing resection of the humerus. This provides the surgeon with improved ability to access the humerus to perform the procedure while avoiding resecting the suprascapularis and infraspinatus muscles. Other instruments in the system are disclosed and provide the surgeon with other advantages such as improved efficiency through reduced complexity and reduced time to perform the procedure. For example, a sizing/visualization instrument is disclosed that has a slot. This slot can facilitate removal of the sizer/visualization instrument from a glenoid reamer anywhere along a longitudinal length of the reamer as opposed to having to remove the sizer/visualization instrument only from an end of the reamer.

Example 1 can include or use subject matter (such as an apparatus, a system, etc.), such as an instrument assembly for a shoulder arthroplasty that can comprise: a cut guide having a slot for aiding a resection of a head of a humerus; and a positioning assembly configured to position the cut guide relative to the head of the humerus, wherein the positioning assembly is configured to couple to a reamer. The positioning assembly can comprise: a boom configured to position the cut guide relative to the reamer and the head of the humerus along a first axis; and an arm coupled to the cut guide and configured to be moveable to position the cut guide relative to the head of the humerus about the reamer in a second axis.

Example 2 can include or use, or can optionally be combined with the subject matter of Example 1, to optionally further comprise an arm holder configured to couple the arm to the boom, the arm holder configured to extend substantially parallel with the reamer when coupled to the boom and configured to be selectively positionally adjustable with respect to the boom.

Example 3 can include or use, or can optionally be combined with the subject matter of Example 2 to optionally include the arm holder includes a plurality, of apertures that are spaced from one another, and wherein the plurality of apertures are each configured to provide a separate location for a fastener to connect the arm with the arm holder and thereby position the arm at a different relative orientation with respect to reamer and the humeral head.

Example 4 can include or use, or can optionally be combined with the subject matter of one or any combination of Example 2 to optionally include the arm is configured to be selectively positionally adjustable with respect to the arm holder, and wherein the arm holder is configured with a plurality of locations for connection with the arm.

Example 5 can include or use, or can optionally be combined with the subject matter of one or any combination of Examples 1 through 4 to optionally include the arm has an arcuate longitudinal length and is selectively positionally adjustable with respect to the reamer by between 0 degrees and 60 degrees of rotation, inclusive.

Example 6 can include or use, or can optionally be combined with the subject matter of one or any combination of Examples 1 through 5 to optionally include wherein the cut guide has a curved shape along a surface interfacing the head of the humerus.

Example 7 can include or use, or can optionally be combined with the subject matter of one or any combination of Examples 1 through 6 to optionally include the first axis is oriented at substantially 45 degrees to a longitudinal axis of the reamer.

Example 8 can include or use, or can optionally be combined with the subject matter of one or any combination of Examples 1 through 7 to optionally include the second axis comprises a curvilinear axis.

Example 9 can include or use subject matter (such as an apparatus, a system, etc.), such as instrument assembly for a shoulder arthroplasty that can comprise: a cut guide having a slot for aiding a resection of a head of a humerus; and a positioning assembly configured to position the cut guide relative to the head of the humerus, wherein the positioning assembly is configured to couple to a reamer. The positioning assembly can comprise: a boom configured to position the cut guide relative to the reamer and the head of the humerus along a first axis; and a cut guide holder coupled to the cut guide and coupled to the boom, the cut guide holder configured to be selectively moveable along a longitudinal length of the boom to position the cut guide relative to the head of the humerus.

Example 10 can include or use, or can optionally be combined with the subject matter of Example 10 to optionally include the first axis is oriented at substantially 45 degrees to a longitudinal axis of the reamer.

Example 11 can include or use, or can optionally be combined with the subject matter of one or any combination of Examples 9 through 10 to optionally include the cut block has a curved shape along a surface interfacing the head of the humerus.

Example 12 can include or use subject matte. (such as an apparatus, a system, etc.), such as cut guide for a shoulder arthroplasty that can comprise: a proximal body portion having a slot therein, wherein the slot is configured to aid a resection of a head of a humerus, wherein the proximal body portion has a plurality of grooves angled and spaced relative to one another at a proximal surface thereof; and a distal body portion connected to the proximal body portion and having plurality of apertures therein, wherein the plurality of apertures are angled and spaced relative to one another; wherein the plurality of apertures are angled in a corresponding manner as the plurality of grooves such that the plurality of apertures have a one-to-one angular correspondence with the plurality of grooves.

Example 13 can include or use, or can optionally be combined with the subject matter of Example 12 to optionally include the proximal body portion is curved and configured to interface with the head of the humerus and the distal body portion is configured to interface with a shaft of the humerus.

Example 14 can include or use, or can optionally be combined with the subject matter of one or any combination of Examples 12 through 13 to optionally include the plurality of apertures and the plurality of grooves are both configured to receive a version guide to set a version of the cut guide relative to a longitudinal axis of the humerus.

Example 15 can include or use, or can optionally be combined with the subject matter of one or any combination of Examples 12 through 14 to optionally include the distal portion has one or more apertures configured to receive a pin to fix the cut guide to the shaft of the humerus.

Example 16 can include or use subject matter (such as an apparatus, a system, etc.), such as system for a shoulder arthroplasty comprising: the cut guide according to Example 12; and a visualization instrument configured to size a glenoid, wherein the visualization instrument is configured to couple with a second reamer via a slot that extends outward from a central aperture configured to receive the second reamer.

Example 17 can include or use, or can optionally be combined with the subject matter of Example 16 to optionally include the visualization instrument is selectively removable from the second reamer anywhere along a longitudinal length thereof via the slot.

Example 18 can include or use subject matter (such as an apparatus, a system, etc.), such as system for a shoulder arthroplasty that can comprise: a cut guide for aiding a resection of a head of a humerus; the positioning assembly according to Example 1 or Example 9; and a visualization instrument configured to size a glenoid, wherein the visualization instrument is configured to couple with a second reamer via a slot that extends outward from a central aperture configured to receive the second reamer.

Example 19 can include or use, or can optionally be combined with the subject matter of Example 18 to optionally include the visualization instrument is selectively removable from the second reamer anywhere along a longitudinal length thereof via the slot.

Each of these non-limiting examples can stand on its own, or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 7 shows the second visualization instrument being removed from a reamer according to an example of the present application.

FIGS. 10A-10C show the cut guide of FIGS. 9A-9D in isolation from the humerus.

DETAILED DESCRIPTION

As discussed herein, orthopedic apparatuses are disclosed herein that facilitate resection and/or sizing of tissue. These apparatuses can be used in combination or in alternative to one another. For example, the visualization guide of FIGS. 6A and 6B or FIGS. 4A and 4B can be used with any of the instrument assemblies or cut guides. Similarly, aspects of the different instrument assemblies described herein can be combined into a single assembly having combined features of the different instrument assemblies. It should be noted that although described in reference to a humerus, the apparatuses and systems of the present application are applicable to other bones or bone portions including the femur and the glenoid, for example.

Figure 1A:
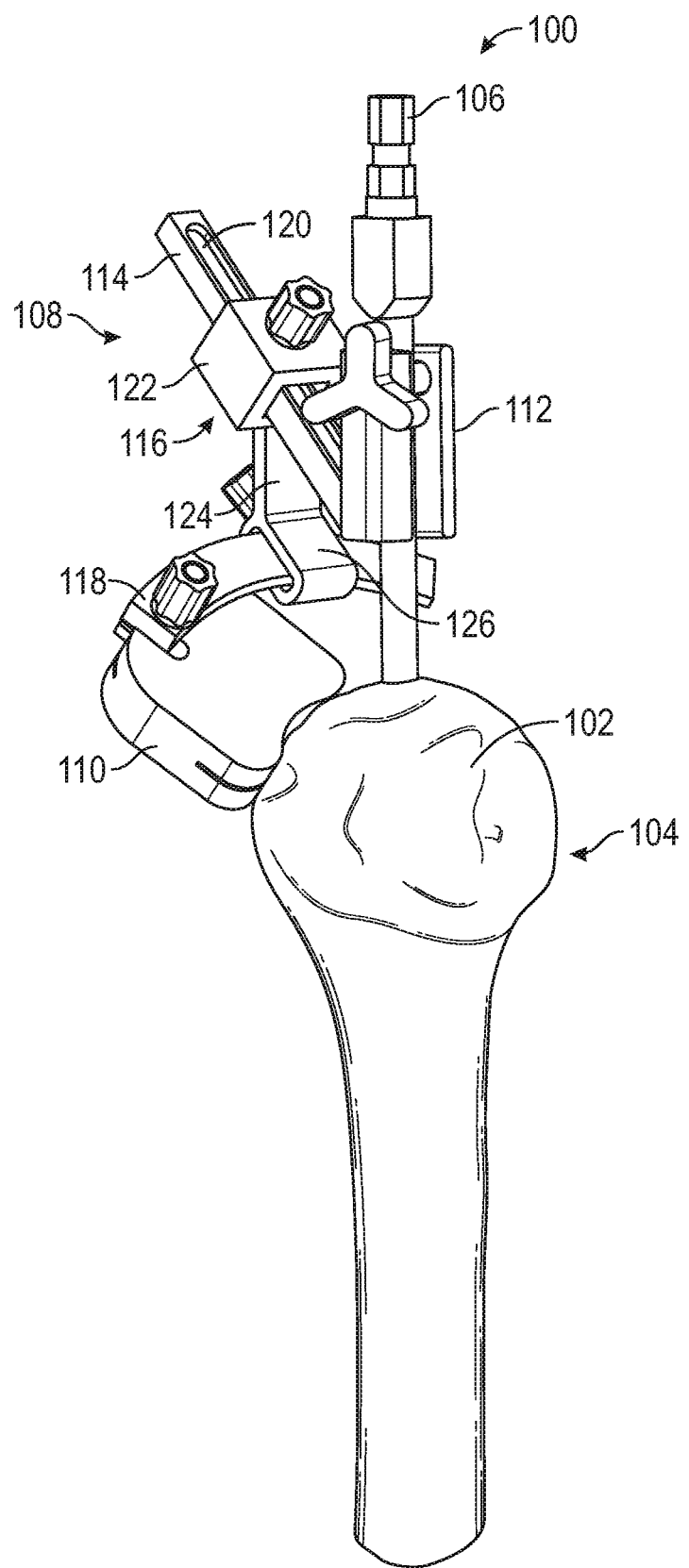
FIGS. 1A-1C are perspective views of a first orthopedic instrument assembly mounted to a humerus via a reamer, the instrument assembly including a cut guide and a positioning assembly according to an example of the present application.
Figure 1B:
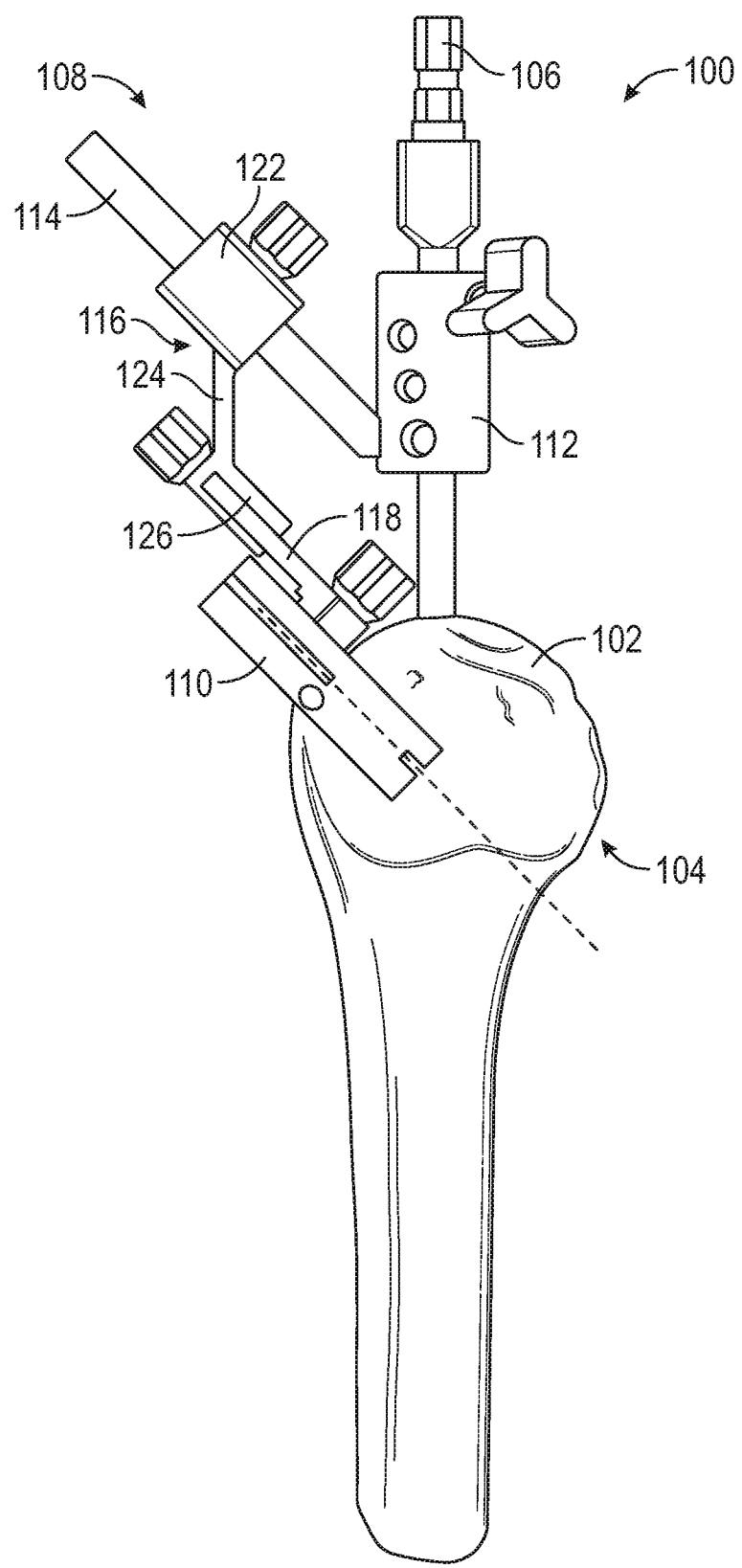
Figure 1C:
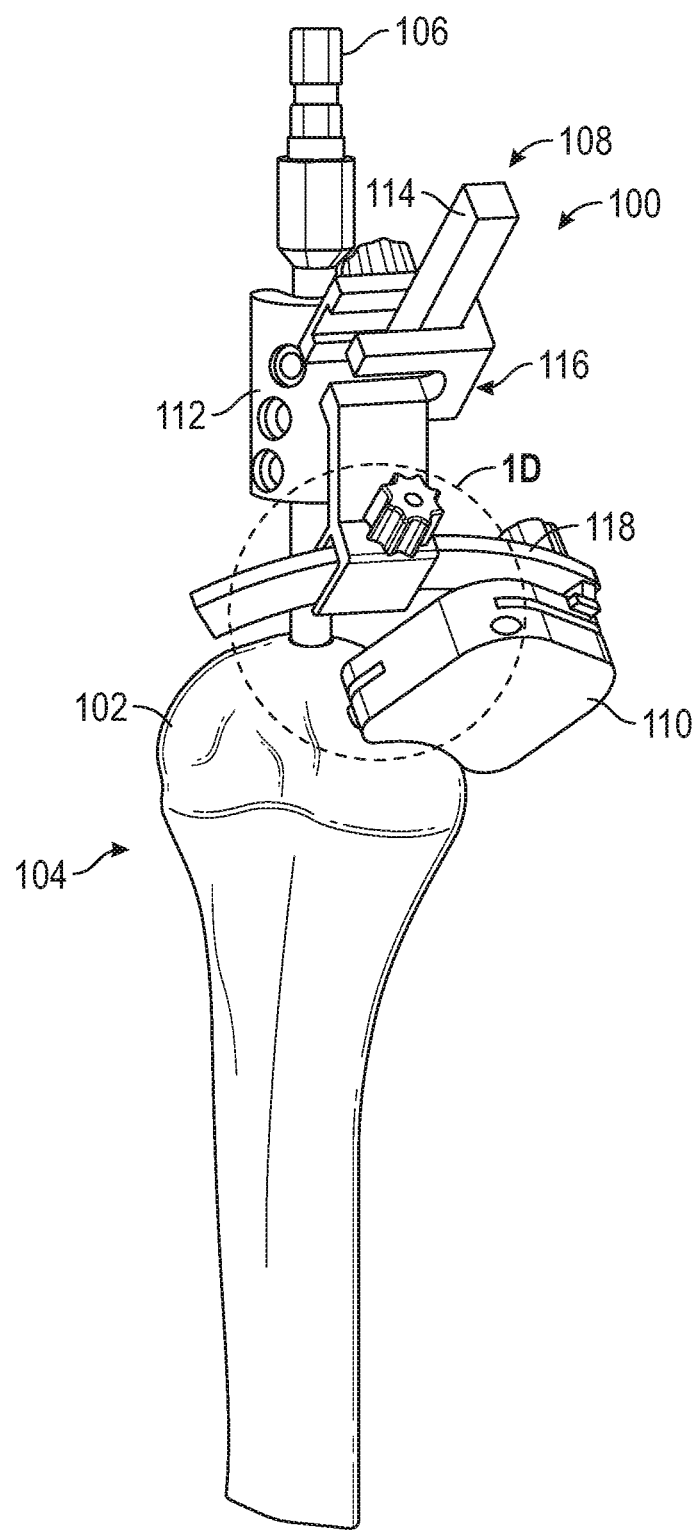

FIGS. 1A-1C show an instrument assembly 100 according to one example. The instrument assembly 100 can used to resect a head 102 of a humerus 104. The instrument assembly 100 can be mounted in position relative to the humerus 104 via a reamer 106. The instrument assembly 100 can include a positioning assembly 108 and a cut guide 110. The positioning assembly 108 can comprise a boom holder 112, a boom 114, an arm holder 116 and an arm 118.

As shown in FIGS. 1A-1C the boom holder 112 can comprise a sleeve type device configured to receive portions of the reamer 106. A fastener such as a thumb screw can connect the boom holder 112 to the reamer 106 in a desired position. The boom holder 112 can have an opening along a longitudinal length thereof to facilitate positioning and removal from the reamer 106.

The boom holder 112 can be connected to the boom 114. According to some examples, such connect can be via a weld or integral connection. However, it is also contemplated another type of connection, keyway, fastener, etc. is contemplated. According to some examples, the boom 114 can be moveable relative to boom holder 112 via a slot or another type of connection feature. The boom 114 can extend radially outwards from the reamer 106 and can extend proximally along a longitudinal length of the reamer 106. Thus, the boom 114 can extend outwards and proximally away from the boom holder 112 and the head 102 of the humerus 104.

The boom 114 can include features such as a slot 120 (FIG. 1A) that can facilitate or aid in coupling and/or position adjustment of the arm holder 116. The arm holder 116 can be positionally adjustable and selectively coupled along a longitudinal length of the boom 114. Thus, the boom 114 along the longitudinal length thereof defines a first axis or first plane of movement relative to the reamer 106 and the head 102 of the humerus 104.

As shown, the arm holder 116 can be configured to couple the arm 118 to the boom 114 such as via a fastener (e.g., thumb screw) or another type of mechanical connection that can facilitate selective movement of the arm 118 and selective connection. The arm holder 116 can be configured with portions that extend substantially parallel with the reamer 106 when coupled to the boom 114. The arm holder 116 can be configured to be selectively positionally adjustable with respect to the boom 114 as described and illustrated. The arm holder 116 can be selectively connected to the arm 118 via a fastener such as a thumb screw or another mechanical mechanism as known in the art that can facilitate positional movement of the arm holder 116 and selective connection with the boom 114. As shown in FIGS. 1A-1B, the arm holder 116 includes a proximal portion 122 configured to facilitate coupling with the boom 114 (e.g., by being shaped as a sleeve or receptacle for example to receive a portion of the boom 114). The arm holder 116 can include an intermediate portion 124 that can extend distally (e.g., substantially parallel with the reamer 106) to a distal portion 126. The distal portion 126 can configured to facilitate selective coupling with the arm 118 (e.g., by being shaped as a sleeve or receptacle for example to receive a portion of the arm 118).

The arm 118 can be configured to be selectively positionally adjustable with respect to the arm holder 116 along a second axis or second plane. This movement is illustrated in FIG. 3 by arrow A. As shown in FIG. 3, the second axis of movement can comprise a curvilinear axis. The curvilinear axis better matches (facilitated by the arcuate shape of the arm 118) the anatomy of the head 102, hick has a curved outer surface (reference FIGS. 2A-2C). The arm 118 can have an arcuate shape along a longitudinal length thereof and can be connected to the cut guide 110 at or adjacent an end thereof. As shown in FIG. 3, the arm 118 can be selectively positionally adjustable with respect to the reamer 106 by between 0 degrees and 60 degrees of rotation, inclusive. However, other degrees of rotation are contemplated such that the arm 118 can be selectively positionally adjustable with respect to the reamer 106 by between 0 degrees and 180 degrees of rotation, inclusive according to further examples. Yet other examples contemplate other varying degrees of rotation about the reamer 106 for the arm 118.

Put another way, the arm holder 116 at the distal portion 126 can include features such as a passage 128 (FIG. 1D) that can facilitate or aid in coupling, retaining and/or positioning of the arm 118. The arm 118 can be positionally adjustable and selectively coupled along a longitudinal length thereof to the arm holder 116. Thus, the arm 118 along the longitudinal length thereof defines a second axis or second plane of movement relative to the reamer 106 and the head 102. As discussed above, the second axis can be curvilinear about an axis defined by the reamer 106 or about another feature such as the humeral head.

Thus, as shown in FIGS. 1A-1C, the instrument assembly 100 can include the cut guide 110 having a slot for aiding a resection of the head 102 of the humerus 104. The instrument assembly 100 can also include the positioning assembly 108, which can be configured to position the cut guide relative to the head 102. The positioning assembly 108 can be configured to couple to the reamer 106 and can include the boom 114 and the arm 118. The boom 114 can be configured to position the cut guide 110 relative to the reamer 106 and the head 102 along the first axis of movement. The arm 118 can be coupled to the cut guide 110 and can be configured to be moveable to position the cut guide 110 relative to the head 102 about the reamer 106 in the second axis of movement.

Figure 1D:
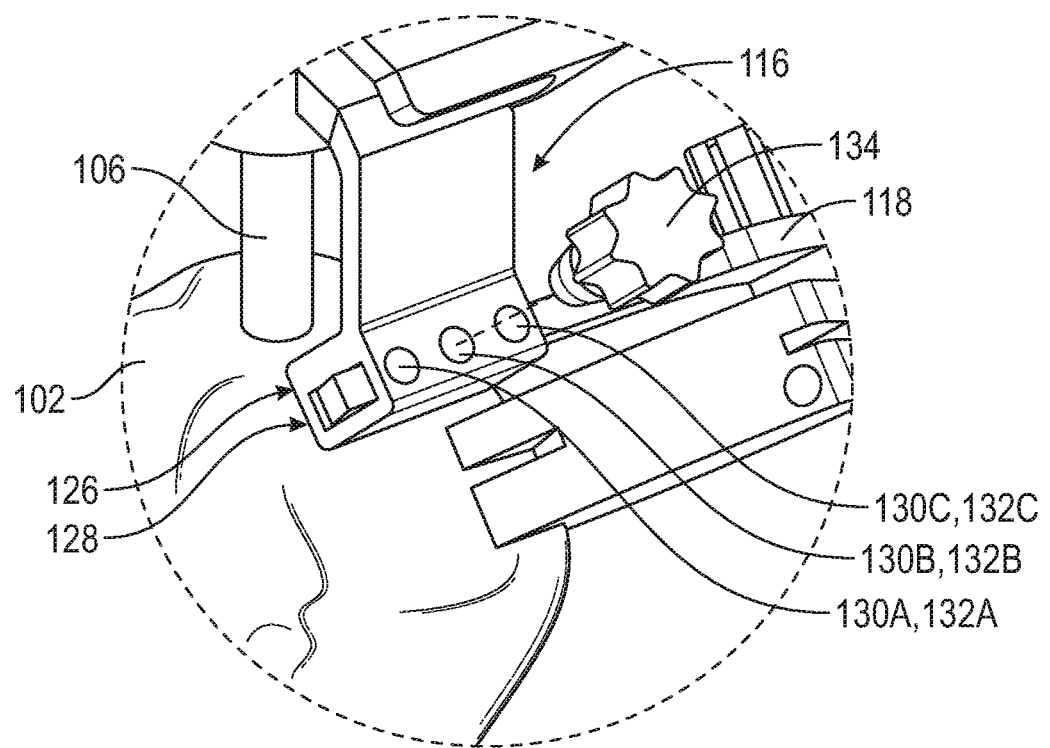
FIG. 1D is an enlarged and exploded view of a portion of the cut guide and positioning assembly of FIG. 1C.

Turning now to FIG. 1D, the arm holder 116 can optionally be configured with a plurality of connection locations 130A, 130B and 130C (here illustrated as apertures 132A, 132B and 132C but in other examples other mechanical features such as projections, slots, etc. are contemplate) the arm 118, Put another way, the arm holder 116 can include the plurality of apertures 132A, 132B and 132C, which can be spaced from one another along a portion of the arm holder 116. These apertures 132A, 132B and 132C can also be angled relative to one another as illustrated in FIGS. 2A-2C, As shown in FIGS. 2A-2C, the plurality of apertures 132A, 132B and 132C can each be configured to provide a separate connection location for a fastener 134 (FIGS. 1C, 1D and 2A-2C) to selectively connect the arm 118 with the arm holder 116, This arrangement can position the arm 118 at various different relative orientations with respect to reamer 106 and the head 102 and can provide for different orientations for the second axis of movement of the arm 118.

Figure 2A:
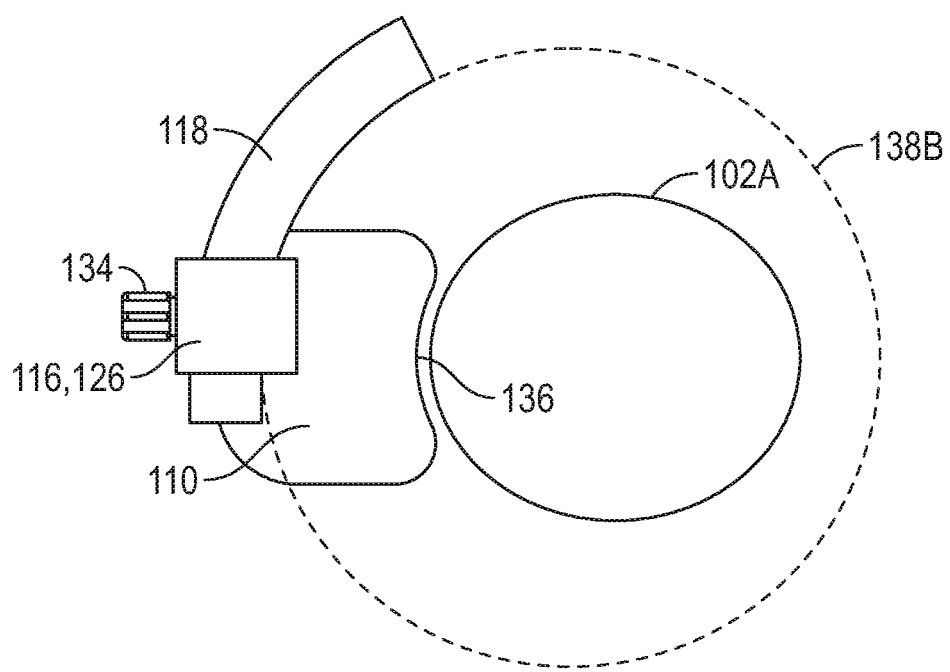
FIG. 2A is schematic view of the cut guide and a portion of the first instrument assembly of FIGS. 1A-1D according to a first example showing an arm holder and an arm of the instrument assembly coupled in a first location corresponding to an average size head of the humerus.
Figure 2B:
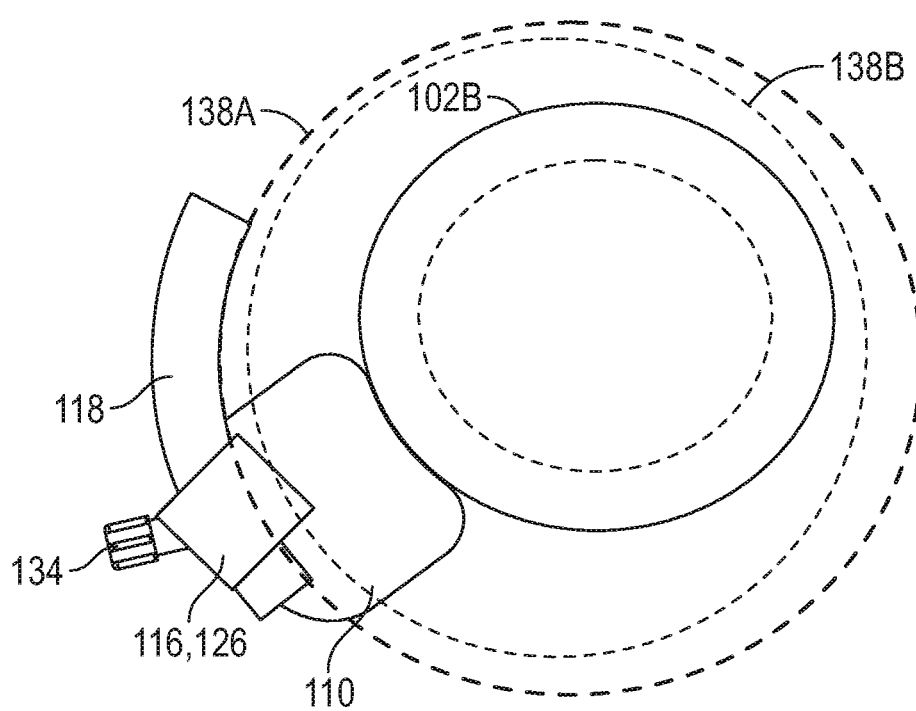
FIG. 2B is schematic view of the cut guide and a portion of the first instrument assembly of FIGS. 1A-1D according to a second example showing the arm holder and the arm of the instrument assembly coupled in a second location corresponding to a larger size head of the humerus.
Figure 2C:
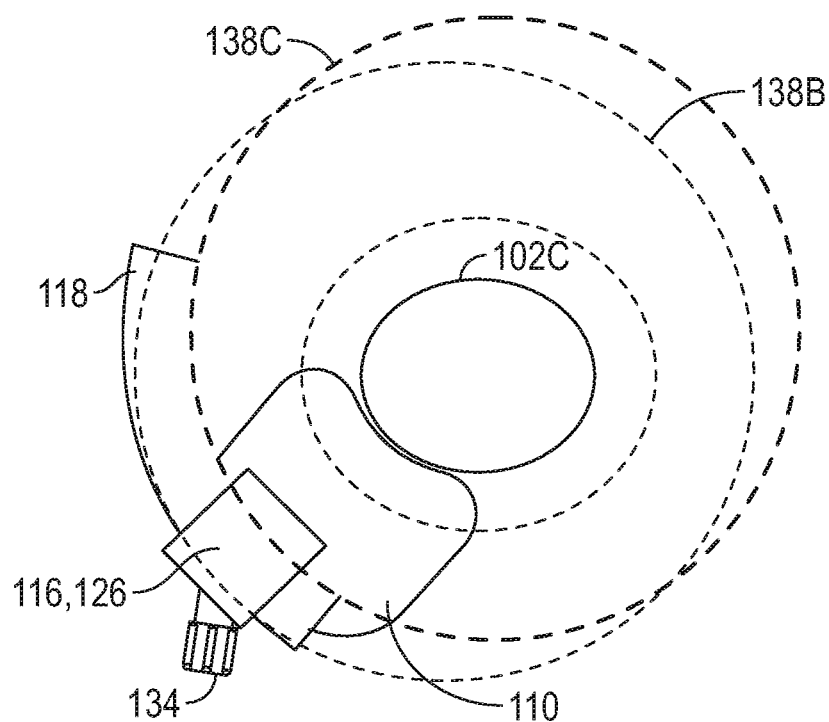
FIG. 2C is schematic view of the cut guide and a portion of the first instrument assembly of FIGS. 1A-1D according to a third example showing the arm holder and the arm of the instrument assembly coupled in a third location corresponding to a smaller size head of the humerus.
Figure 3:
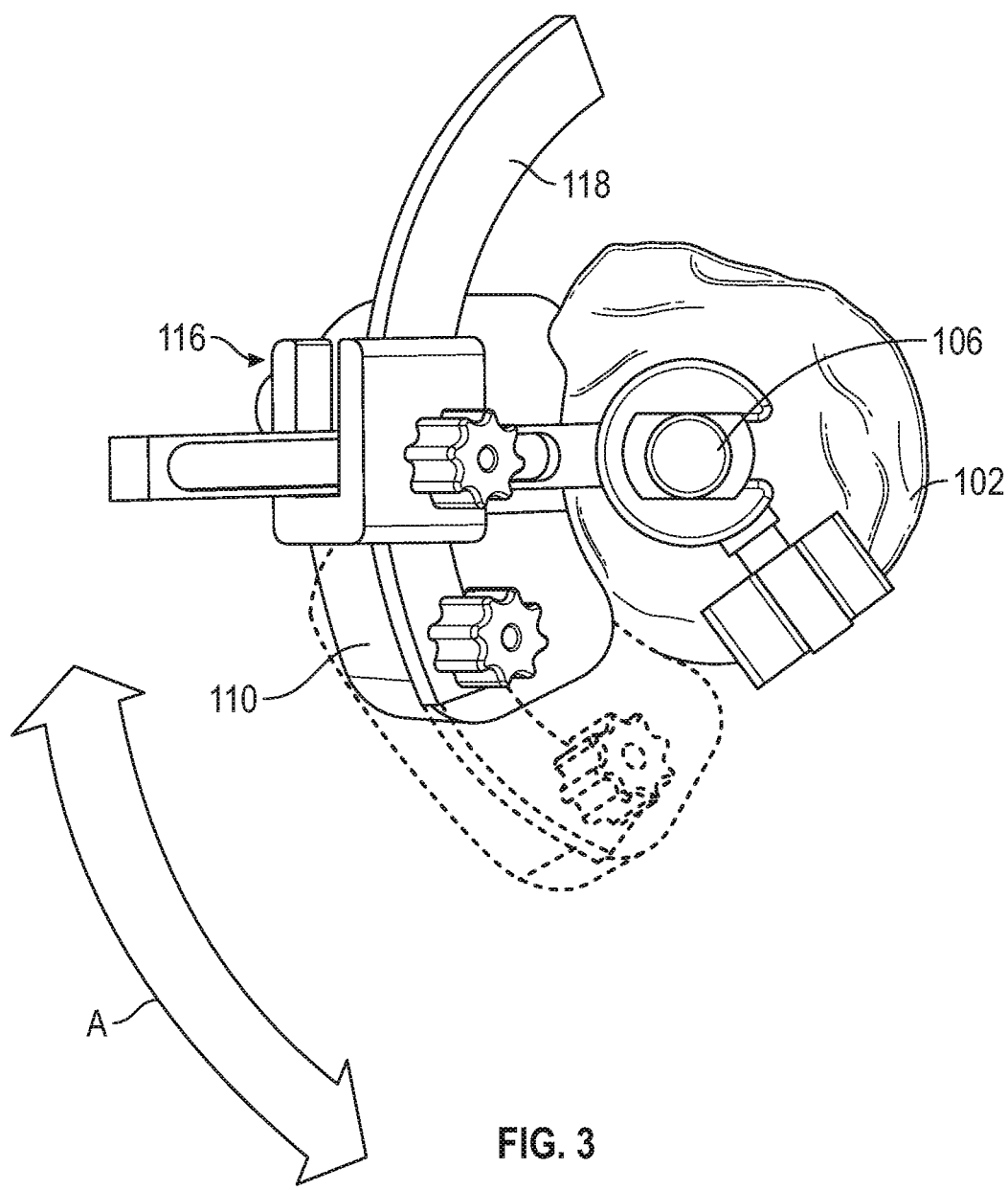
FIG. 3 is a plan view of the instrument assembly of FIGS. 1A-1D having the arm and the cut guide rotated about the reamer to any desired angle between 0 degrees and 60 degrees, inclusive according to an example of the present application.

FIGS. 2A to 2C show various examples using the fastener 134 received in a different one of the plurality of apertures 132A, 132B and 132C (FIG. 1D). FIGS. 2A to 2C illustrate the cut guide 110 can have a curved shape along a surface 136 interfacing with the head 102 of the humerus 104. This shape can allow the cut guide 110 to better conform to the various shapes of the head 102A, 102B or 102C as illustrated in FIGS. 2A to 2C.

FIG. 2A shows the distal portion 126 of the arm holder 116 and the arm 118 connected by the fastener 134 received the aperture 132B (the second connection location 130B of FIG. 1D). The fastener 134 positioned in is this connection location corresponds to an average size head 102A of the humerus. The second axis 138B of the arrangement of FIG. 2A is illustrated by a dashed line in FIG. 2A. As shown in FIG. 2A, the second axis 138B is curvilinear about the average size head 102A.

FIG. 2B shows the distal portion 126 of the arm holder 116 and the arm 118 connected by the fastener 134 received the aperture 132A (the second connection location 130A of FIG. 1D). The fastener 134 positioned in is this connection location corresponds to a larger size head 102B of the humerus 104 (the average size head 102A is illustrated in phantom in FIG. 2B). The second axis 138A of the arrangement of FIG. 2B is illustrated by a second dashed line in FIG. 2B. The second axis 138B corresponding to the average size head is also illustrated for reference in FIG. 2B. As shown in FIG. 2B, the second axis 138A has a different orientation and path than the second axis 138B. Indeed, as shown in FIG. 2B, the arm 118 has a different orientation with respect to the head 102B and the reamer (not shown) than the arm 118 of FIG. 2A. In the example of FIG. 2B, the second axis 138A is curvilinear about the larger size head 102B. The radius of the circular path of FIG. 2B can be the same as or different than that of the circular path of FIG. 2A.

FIG. 2C shows the distal portion 126 of the arm holder 116 and the arm 118 connected by the fastener 134 received the aperture 132C (the second connection location 130C of FIG. 1D), The fastener 134 positioned in is this connection location corresponds to a smaller size head 102C of the humerus 104 (the average size head 102A is illustrated in phantom in FIG. 2C). The second axis 138C of the arrangement of FIG. 2C is illustrated by a second dashed line in FIG. 2C. The second axis 138B corresponding to the average size head is also illustrated for reference in FIG. 2C. As shown in FIG. 2B, the second axis 138C has a different orientation and path than the second axis 138B. Indeed, as shown in FIG. 2C, the arm 118 has a different orientation with respect to the head 102C and the reamer (not shown) than the arm 118 of FIG. 2A or FIG. 2B. In the example of FIG. 2C, the second axis 138C is curvilinear about the smaller size head 102C, The radius of the circular path of FIG. 2B can be the same as or different than that of the circular path of FIG. 2A.

Figure 4A:
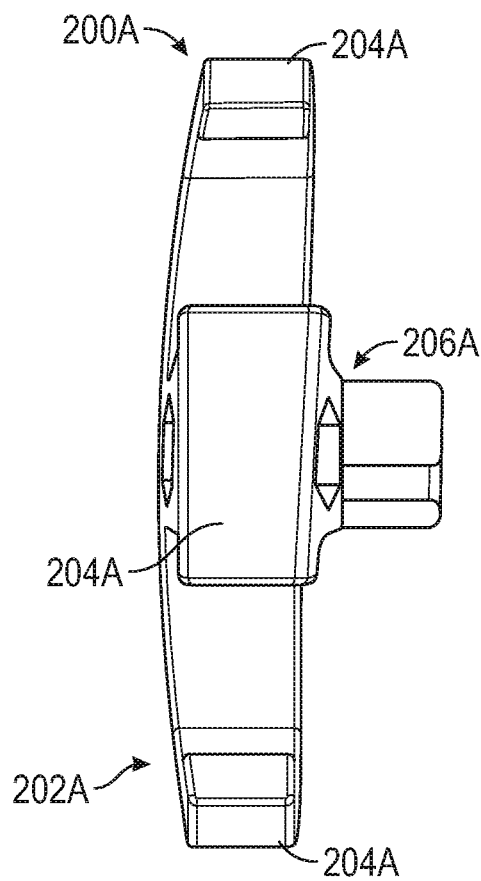
FIGS. 4A and 4B are plan views of a first visualization instrument that can be used to size a glenoid according to an example of the present application.
Figure 4B:
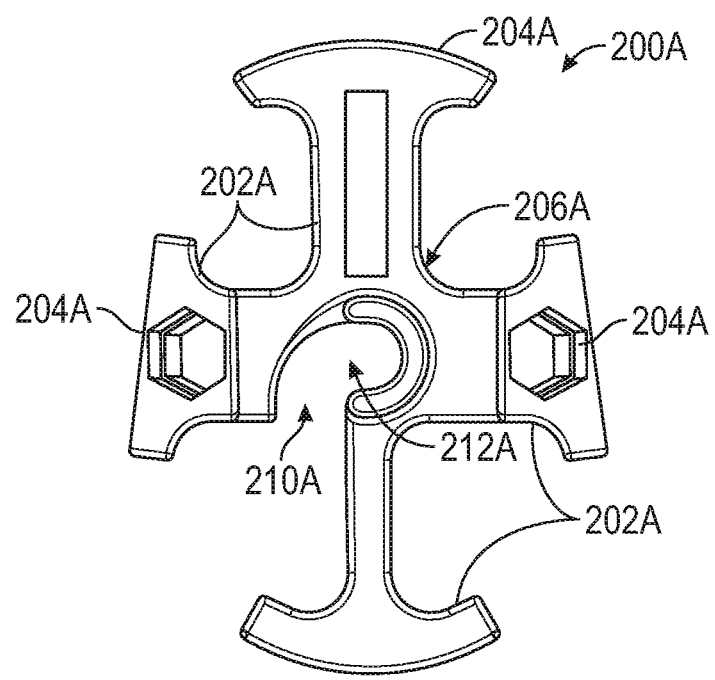

FIGS. 4A and 4B show an example of a visualization instrument 200A according to one example. The visualization instrument 200A can include wings 202A the outer edge 204A of which can be shaped to match a geometry of a glenoid of the patient. The visualization instrument 200A can include a central hub 206A located between and connecting to the wings 202A. The central hub 206A can be configured to be grasped by the surgeon, with the surgeon's fingers being positioned around the wings 202A. Alternatively, a dedicated instrument configured to engage and grasp the visualization instrument 200A can be utilized.

The visualization instrument 200A can be configured to size a glenoid by being provided in different stock sizes as a system, and by having the wings 202A, the outer edge 204A of which is shaped to match the geometry of the glenoid of the patient. Thus, the surgeon can select the instrument 200A of a proper size to match the instrument 200A with the rim of the glenoid along the outer edge 204A when the visualization instrument 200A is located on a reamer 208 (FIG. 5) inserted in a geometric center of the glenoid.

Figure 5:
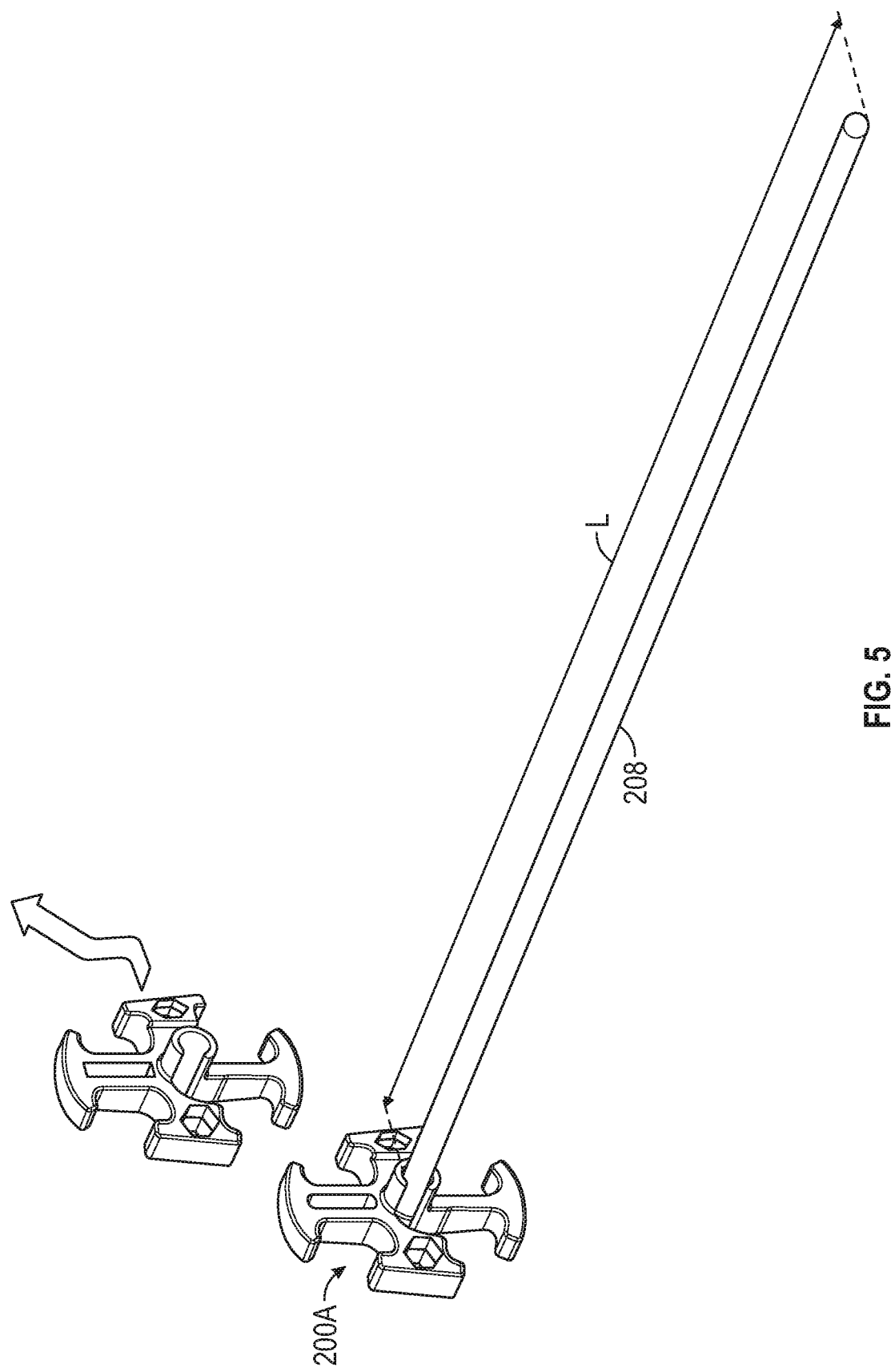
FIG. 5 shows the first visualization instrument being removed from a reamer according to an example of the present application.

As shown in FIG. 4B and FIG. 5, the visualization instrument 200A, and in particular the central hub 204A, can be configured to receive and couple with the second reamer 208 via a slot 210A that extends outward from a central aperture 212A. The central aperture 212A can be configured to receive the second reamer 208. Thus, as shown in FIG. 4B, the slot 210A can communicate with the central aperture 212A and can communicate via an opening in an outer edge of the central hub 204A. In the example of FIG. 4B, the slot 210A can have an arcuate path.

As shown in FIG. 5, the visualization instrument 200A can be configured to be selectively insertable and removable from the second reamer 208 via the slot 210A anywhere along a longitudinal length L thereof. Put another way, the visualization instrument 200A need not be inserted and/or removed from only an end of the second reamer 208 but can be removed and/or inserted along any portion of the length thereof via the slot 210A (FIG. 4B).

Figure 6A:
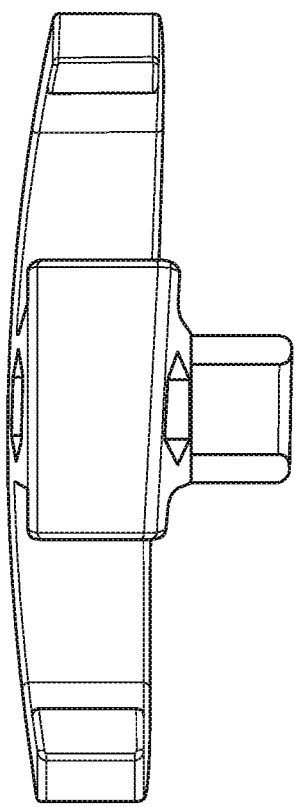
FIGS. 6A and 6B are plan views of a second visualization instrument that can be used to size the glenoid according to an example of the present application.
Figure 6B:
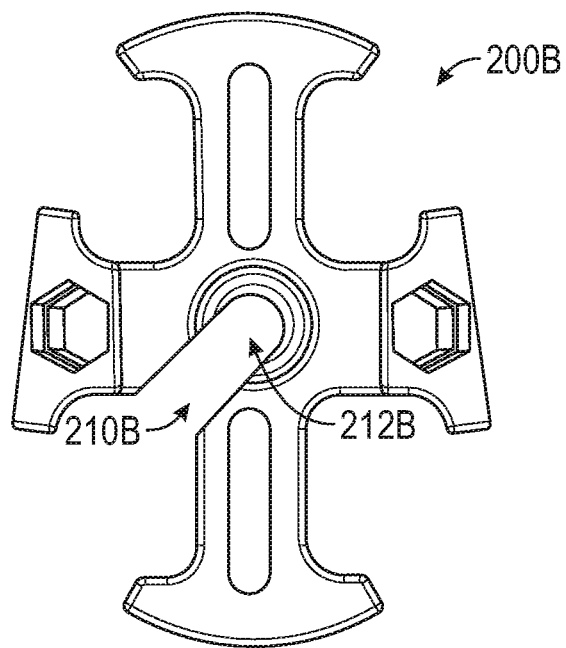

FIGS. 6A-7 show an alternative example of a visualization instrument 200B that differs from the visualization instrument of FIGS. 4A-5. The difference in the visualization instrument 200B is that a slot 210B can extend radially outward from the central aperture 212B rather than having a curved path as is the case in the example of FIGS. 4A-5.

Figure 8A:
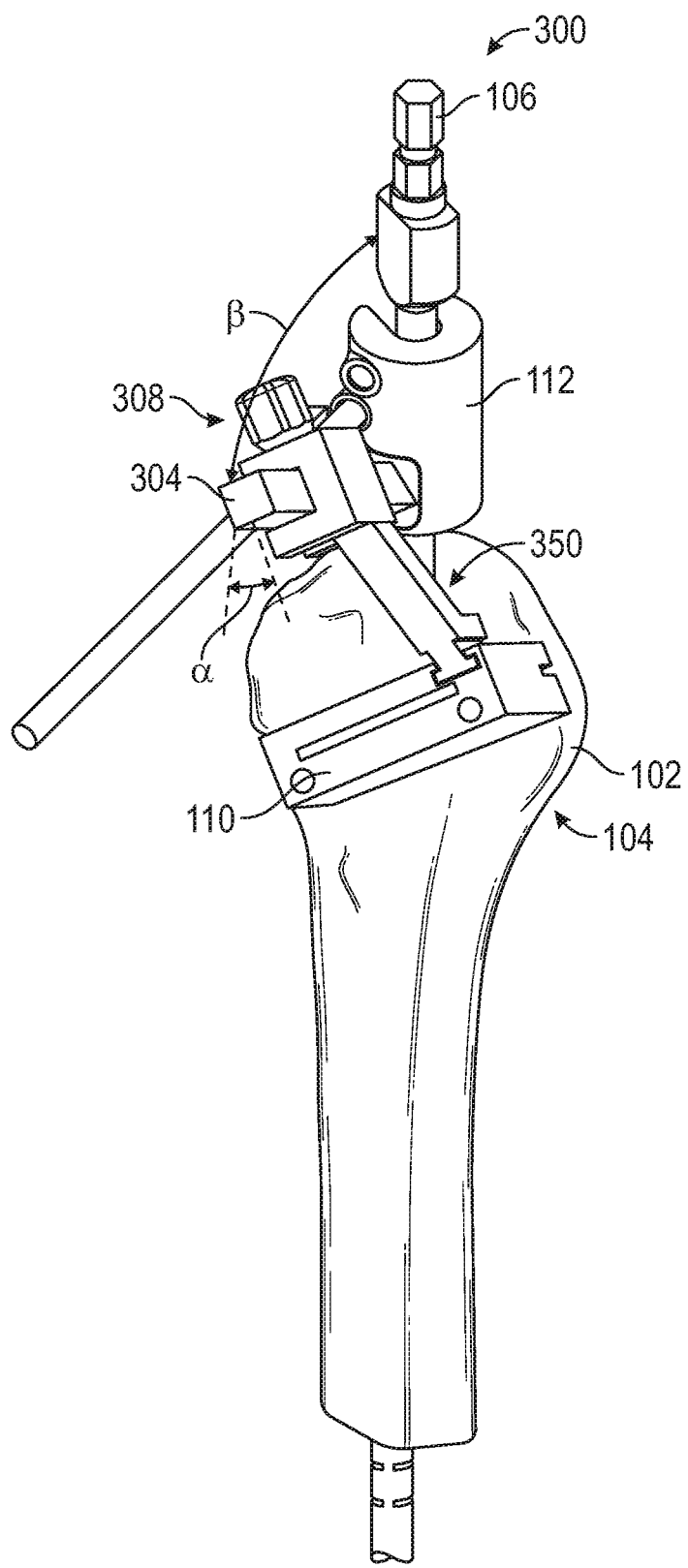
FIGS. 8A-8C are perspective views of a second orthopedic instrument assembly mounted to a humerus via a reamer, the instrument assembly including a cut guide and a positioning assembly according to an example of the present application.
Figure 8B:
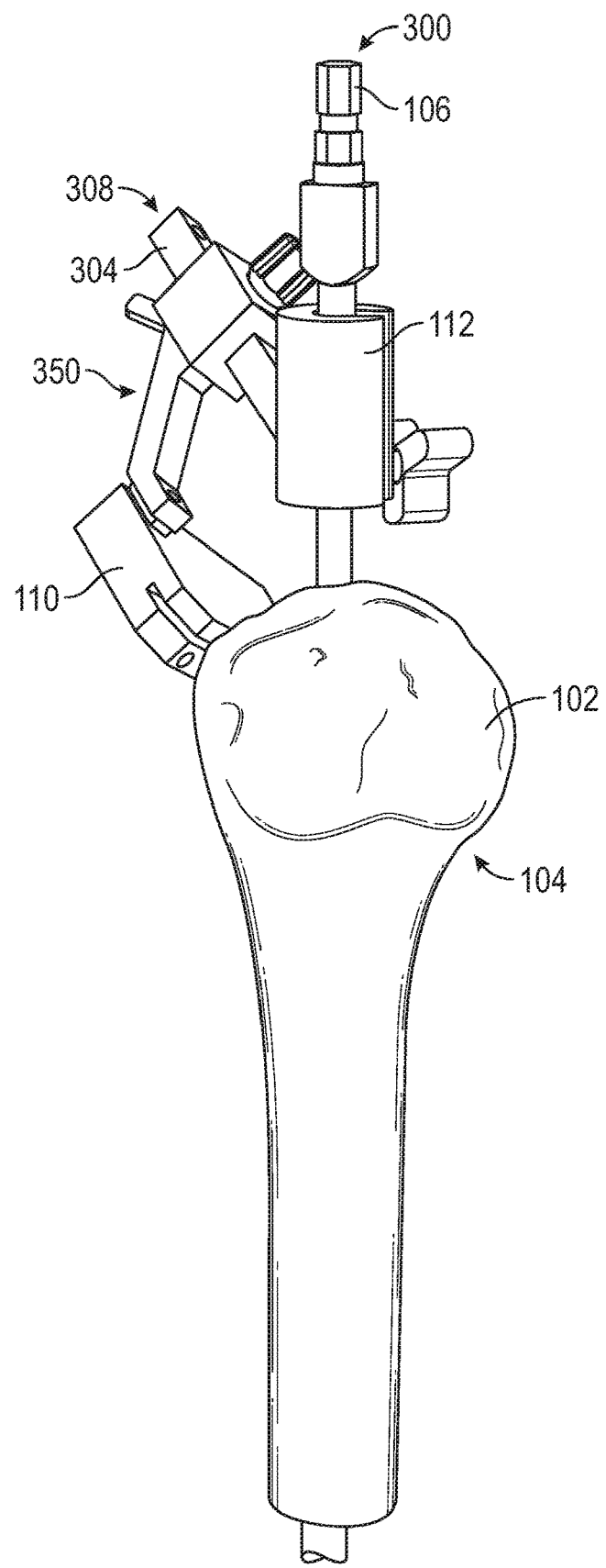
Figure 8C:
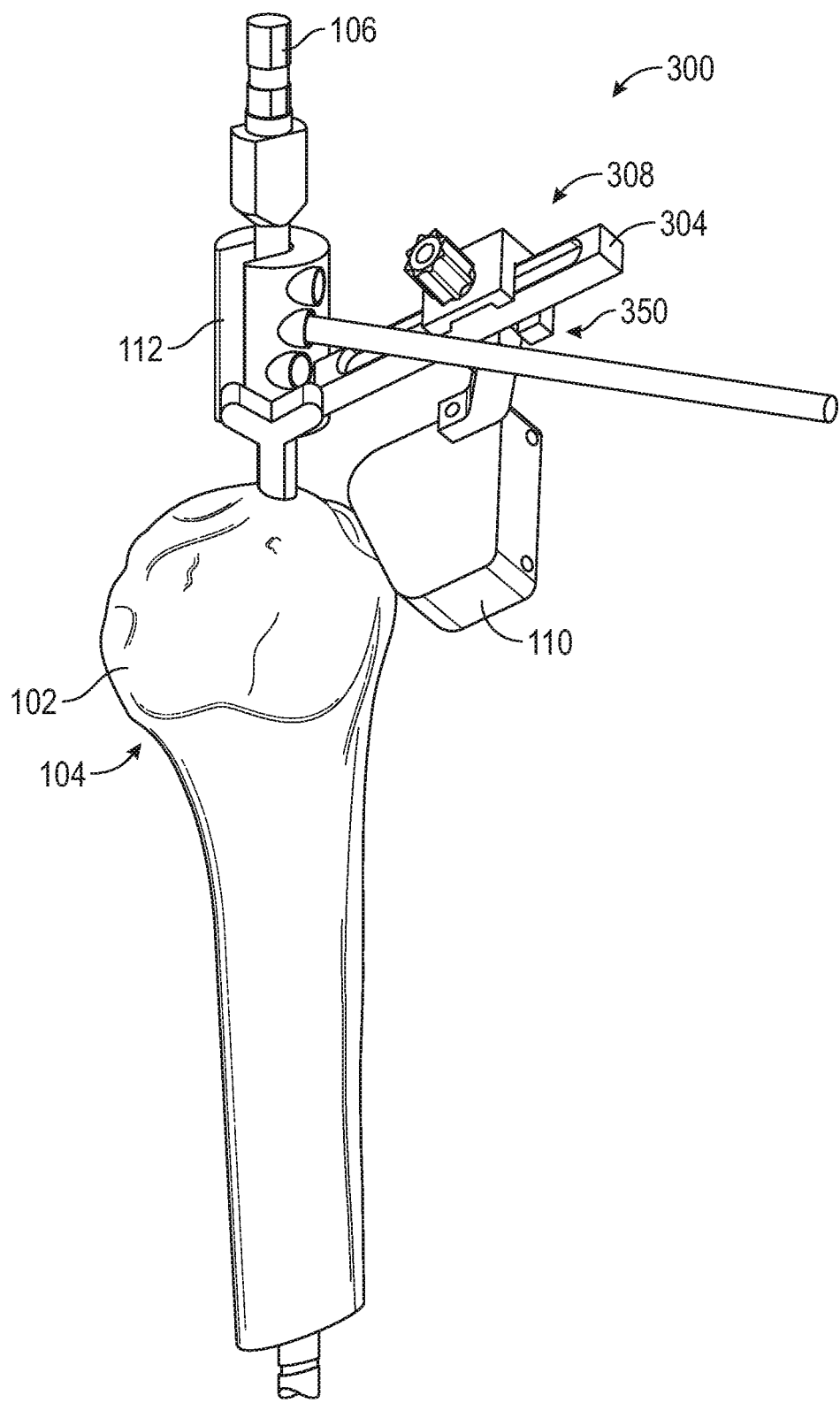

FIGS. 8A-8C show an instrument assembly 300 according to another example. The instrument assembly 300 can be constructed in a manner similar to that of the instrument assembly 100 of FIGS. 1A-1D with some differences as noted below. Thus, the instrument assembly 300 can used to resect the head 102 of the humerus 104 as previously discussed. The instrument assembly 300 can be mounted in position relative to the humerus 104 via the reamer 106. The instrument assembly 300 can include a positioning assembly 308 and the cut guide 110. The positioning assembly 308 can comprise the boom holder 112, a boom 314, a cut guide holder 350.

As compared with the instrument assembly 100, the instrument assembly 300 lacks an arm 118 (FIGS. 1A-1D) coupling the instrument assembly with the cut guide 110. Rather, the cut guide holder 350 can be directly connected with both the boom 314 and the cut guide 110. The cut guide holder 350 can be selectively moveable along a longitudinal length of the boom 314 to adjust a position of the cut guide 110 in a manner previously described with regard to the arm holder 116 of FIGS. 1A-1D. The cut guide holder 350 can be configured to receive a portion of the boom 314 in a channel or other female feature, for example. A fastener such as a thumb screw can be used to selectively connect the cut guide holder 350 with the boom 314.

As shown in FIGS. 8A-8C, the boom 314 can be modified from the boom 114 of FIGS. 1A-1C in that the boom 314 can be clocked at an angle α (shown in FIG. 8A) in addition to an angle β with respect to an axis A of the reamer 106. This angle α can comprise any desired angle. In the example of FIGS. 8A-8C the angle can be substantially 45 degrees. This arrangement can provide that the first axis of movement as defined by the boom 314 is oriented at substantially 45 degrees to the axis A of the reamer 106. This arrangement can also orient the cut guide 110 via the cut guide holder 350 at substantially 45 degrees with respect to the axis A of the reamer 106.

FIGS. 9A-10C show a cut guide 400 for a shoulder arthroplasty. The cut guide 400 can include a proximal body portion 402 and a distal body portion 404. The proximal body portion 402 can include a slot 406, a proximal surface 408 and a plurality of grooves 410A, 410B and 410C. The distal body portion 404 can include a plurality of apertures 412A, 412B and 412O.

The proximal body portion 402 and the distal body portion 404 can be connected together such as by an integral or other connection. Thus, the cut guide 400 can comprise single piece component according to some examples including those of FIGS. 9A-10C.

Figure 9A:
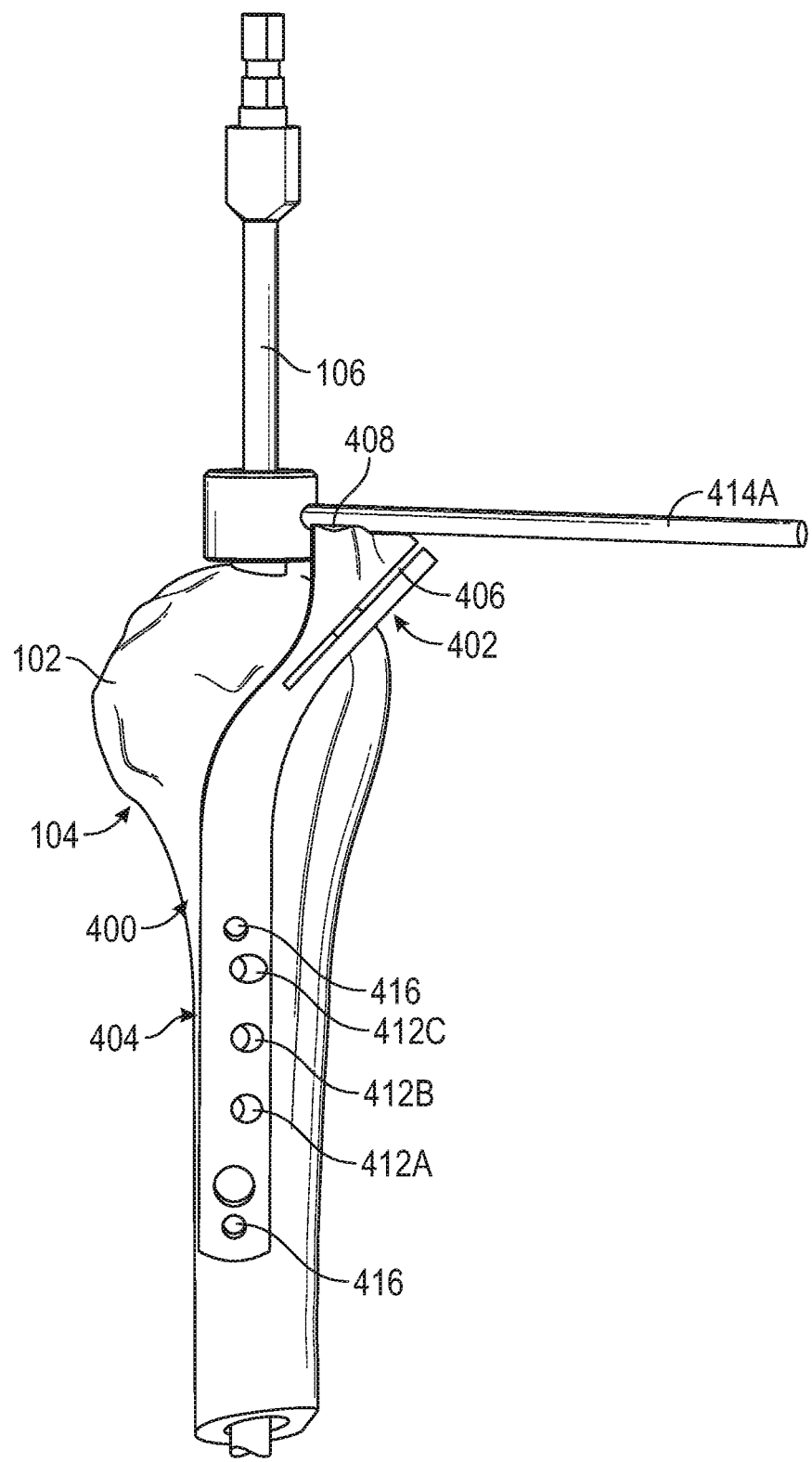
FIGS. 9A and 9B are perspective views of a cut guide mounted to a humerus, the cut guide configured to interact with one or more version guides according to an example of the present application.
Figure 9B:
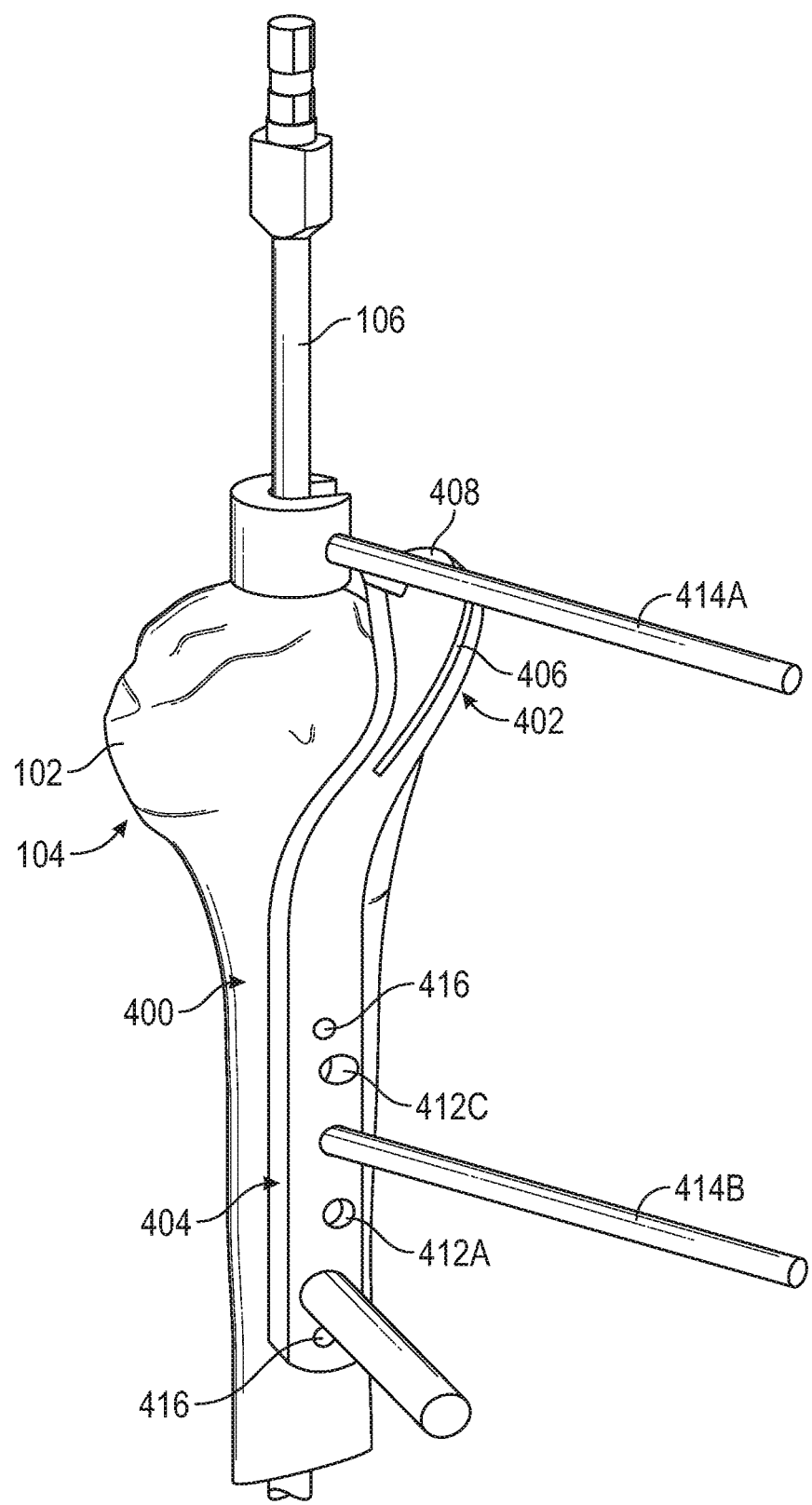
Figure 9C:
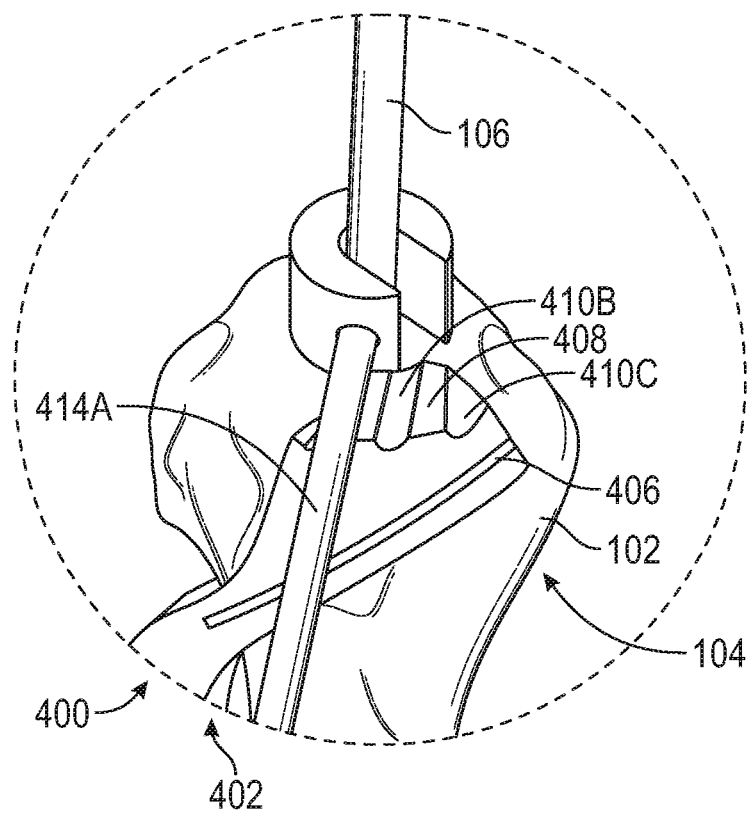
FIG. 9C is an enlargement of a proximal portion of the cut guide of FIG. 9B.
Figure 10C:
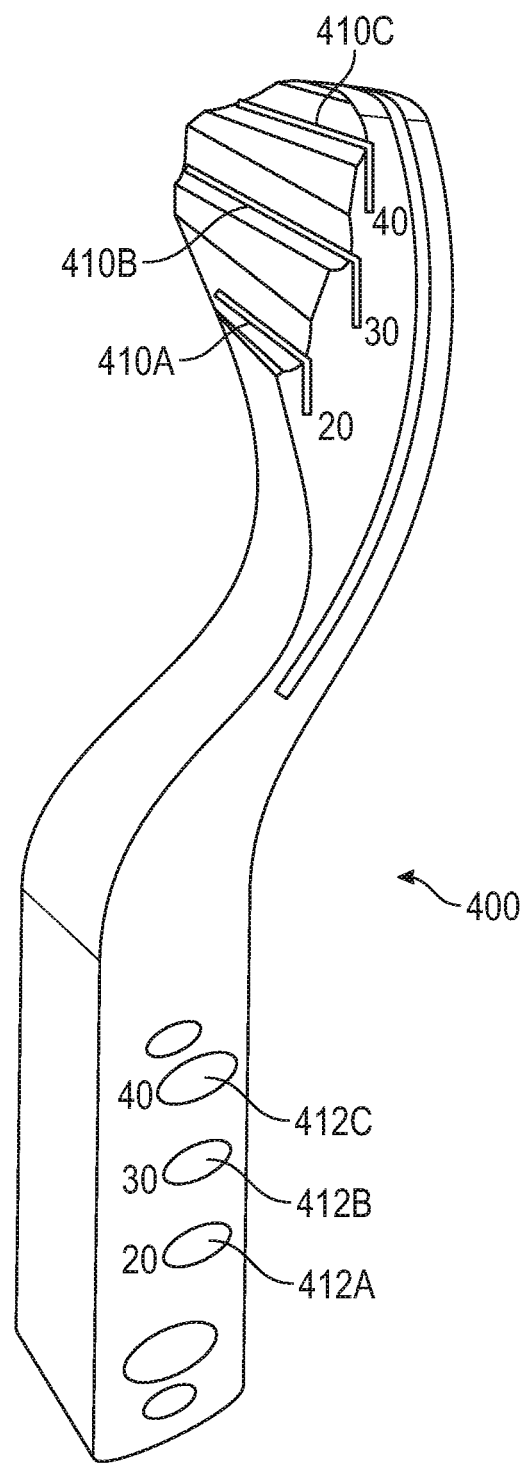

The proximal body portion 402 can define the slot 406 therein. The slot 406 can be configured to aid a resection of the head 102 of the humerus 104 as previously discussed. The proximal body portion 402 can be curved and can be configured to interface with the head 102 of the humerus 104. The plurality of grooves 410A, 410B and 410C of the proximal body portion 402 can be angled and spaced relative to one another at the proximal surface 408 as best shown in FIGS. 9C, 10A and 10C. As shown in FIGS. 9A-9C, the cut guide 400 can be positioned relative to the humerus 104 and the reamer 106 to interact with a first version guide 414A. As illustrated, the first version guide 414A can be coupled to the reamer 106 and can extend outwards therefrom to seat in one of the plurality of grooves 410A, 410B and 410C of the proximal surface 408. This arrangement can be used to check and orient the cut guide 400 with a desired version (orientation). As illustrated in FIGS. 9C and 10C, the plurality of grooves 410A, 410B and 410C can be positioned and angled relative to one another and the reamer 106 (when the cut guide 400 is mounted) to provide for different angles of version (e.g. 20 degrees, 30 degrees, 40 degrees, etc.). It should be noted that although three grooves are illustrated, other numbers of grooves comprising the plurality of grooves 410A, 410B and 410C are contemplated.

The distal body portion 404 can be configured to interface with a shaft of the humerus 404. The distal body portion 404 can have the plurality of apertures 412A, 412B and 412C defined therein. Additionally, the distal body portion 404 can define one or more apertures 416 configured to receive a pin to fix the cut guide 400 to the shaft of the humerus 104.

The plurality of apertures 412A, 412B and 412C can each be configured to receive a second version guide 414B therein as shown in FIG. 9B. Thus, the plurality of apertures 412A, 412B and 412C and the plurality of grooves 410A, 410B and 410C can both be configured to receive a version guide to set a version of the cut guide relative to a longitudinal axis of the humerus (here defined by the longitudinal axis A of the reamer 106).

Figure 9D:
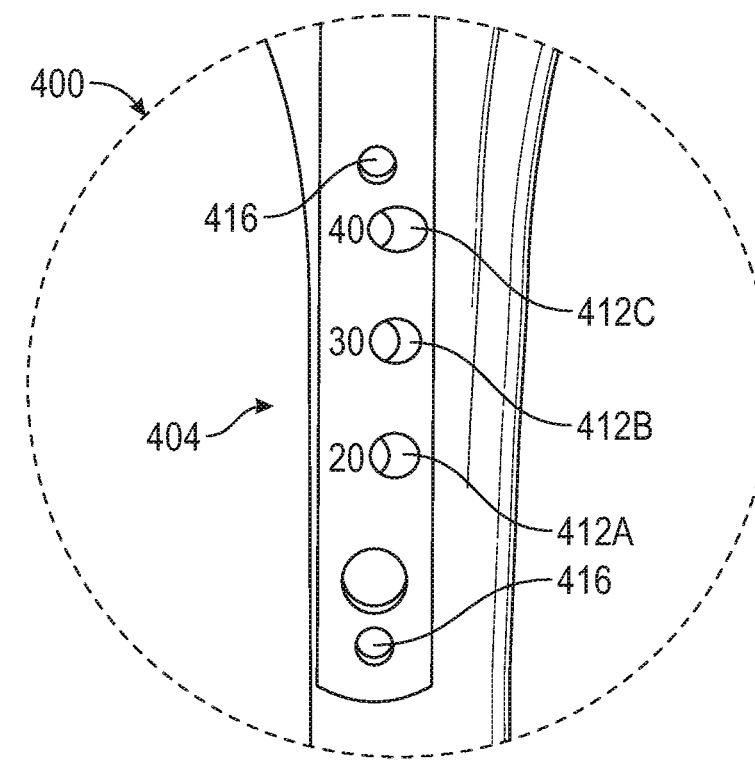
FIG. 9D is an enlargement of a distal portion of the cut guide of FIG. 9A.

As shown in FIGS. 9D and 10C, the plurality of apertures 412A, 412B and 412C can be angled and spaced relative to one another and with respect to the reamer 106 when the cut guide 400 is mounted. The plurality of apertures 412A, 412B and 412C can be positioned and angled relative to one another and the reamer 106 (when the cut guide 400 is mounted) to provide for different angles of version (e.g. 20 degrees, 30 degrees, 40 degrees, etc.). It should be noted that although three apertures are illustrated, other numbers of apertures comprising the plurality of apertures 412A, 412B and 412C are contemplated.

In the example of FIGS. 9A-10C, the plurality of apertures 412A, 412B and 412C can be angled in a corresponding manner (e.g., a same orientation) as the plurality of grooves 410A, 410B and 410C such that the plurality of apertures 412A, 412B and 412C can have a one-to-one angular correspondence with the plurality of grooves 410A, 410B and 410C. Put another way, the aperture 412A can have a same angle (e.g., 20 degrees) as the groove 410A. Similarly, the aperture 412B can have a same angle (e.g., 30 degrees) as the groove 410B. The aperture 412C can have a same angle (e.g., 40 degrees) as the groove 410C.

It should be noted that it is contemplated in other examples that the plurality of apertures 412A, 412B and 412C can be angled in a different manner from the plurality of grooves 410A, 410B and 410C, Thus, for example apertures 412A, 412B and 412C can be provided at, for example 25 degrees, 35 degrees, 45 degrees, respectively, while the grooves 410A, 410B and 410C can be provided at, for example 20 degrees, 30 degrees, 40 degrees, respectively.

VARIOUS NOTES

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more Examples thereof), either with respect to a particular example (or one or more Examples thereof), or with respect to other examples (or one or more Examples thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "of" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "substantially round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more Examples thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An instrument assembly for a shoulder arthroplasty comprising:
    a cut guide having a slot for aiding a resection of a head of a humerus; and
    a positioning assembly configured to position the cut guide relative to the head of the humerus, wherein the positioning assembly is configured to couple to a reamer positioned in a medullary canal of the humerus, wherein the positioning assembly comprises:
    a boom extending along a first axis and configured to position the cut guide relative to the reamer and the head of the humerus along the first axis, wherein the first axis is oriented at an acute angle to a longitudinal axis of the reamer;
    an arm extending along a second curvilinear axis and coupled to the cut guide, wherein the arm is configured to be slidably moveable relative to the boom to position the cut guide relative to the head of the humerus about the reamer along the second curvilinear axis, wherein the arm has an arcuate longitudinal length configured to partially extend around the head of the humerus and is selectively positionally adjustable with respect to the reamer by between 0 degrees and 60 degrees of rotation, inclusive;
    an arm holder configured to couple the arm to the boom, the arm holder configured to extend substantially parallel with the reamer when coupled to the boom and configured to be selectively positionally adjustable with respect to the boom; and
    a boom holder coupling the boom to the reamer, wherein the boom holder is selectively positionally adjustable and securable with respect to the reamer to be moveable along an elongate length of the reamer.

2. The instrument assembly of claim 1, wherein the arm holder includes a plurality of apertures that are spaced from one another, and wherein the plurality of apertures are each configured to provide a separate location for a fastener to connect the arm with the arm holder and thereby position the arm at a different relative orientation with respect to reamer and the humeral head.

3. The instrument assembly of claim 1, wherein the arm is configured to be selectively positionally adjustable with respect to the arm holder, and wherein the arm holder is configured with a plurality of locations for connection with the arm.

4. The instrument assembly of claim 1, wherein the cut guide has a curved shape along a surface interfacing the head of the humerus.

5. The instrument assembly of claim 1, wherein the first axis is oriented at substantially 45 degrees to a longitudinal axis of the reamer.

6. A system comprising:
    the instrument assembly for the shoulder arthroplasty of claim 1; and
    a visualization instrument configured to size a glenoid, wherein the visualization instrument is configured to couple with a second reamer via a slot that extends outward from a central aperture configured to receive the second reamer.

7. The system of claim 6, wherein the visualization instrument is selectively removable from the second reamer anywhere along a longitudinal length thereof via the slot.

* * * * *